United States Patent [19]

Walker

[11] Patent Number: 5,419,176

[45] Date of Patent: May 30, 1995

[54] PARTICLE DETECTION AND ANALYSIS

[75] Inventor: Malcolm J. Walker, Lichfield, United Kingdom

[73] Assignee: Rig Technology Limited, Aberdeen, Scotland

[21] Appl. No.: 142,382

[22] PCT Filed: May 20, 1992

[86] PCT No.: PCT/GB92/00917

§ 371 Date: Jan. 7, 1994

§ 102(e) Date: Jan. 7, 1994

[87] PCT Pub. No.: WO92/21021

PCT Pub. Date: Nov. 26, 1992

[30] Foreign Application Priority Data

May 21, 1991 [GB] United Kingdom ............... 9111008

[51] Int. Cl.$^6$ ............................................. G01N 3/00
[52] U.S. Cl. ............................. 73/12.11; 73/12.05
[58] Field of Search ............... 73/12.05, 12.09, 12.11, 73/12.12, 579

[56] References Cited

U.S. PATENT DOCUMENTS

| | | | |
|---|---|---|---|
| 3,418,546 | 12/1968 | Beavers et al. | 73/12.05 X |
| 3,557,616 | 1/1971 | Landon, Jr. et al. | 73/DIG. 4 |
| 3,587,291 | 6/1971 | Escallier et al. | 73/12.05 |
| 3,805,591 | 4/1974 | Willis et al. | 73/12.05 X |
| 3,844,174 | 10/1974 | Chabre | 73/DIG. 4 |
| 4,184,372 | 1/1980 | Brown | 73/12.09 |
| 4,770,527 | 9/1988 | Park | 73/12.05 X |
| 4,807,482 | 2/1989 | Park et al. | 73/DIG. 4 |
| 5,113,680 | 5/1992 | Matsura et al. | 73/12.11 X |
| 5,144,251 | 9/1992 | Fasching et al. | 73/861.73 X |

FOREIGN PATENT DOCUMENTS

62-23902 10/1987 Japan ................... 73/12.12

Primary Examiner—Richard E. Chilcot, Jr.
Assistant Examiner—Elizabeth L. Dougherty
Attorney, Agent, or Firm—Lee, Mann, Smith, McWilliams, Sweeney & Ohlson

[57] ABSTRACT

The invention provides a method of, and apparatus for detecting and analyzing moving particles using an impact responsive transducer which generates a detection signal having an amplitude related to force of particle impact. The transducer output signal is monitored and when it exceeds a given threshold, any local maximum values are noted. Those values are compared to determine which has the overall maximum amplitude. A final signal is then generated in order to provide a representation of the maximum value, and hence the momentum and time occurrence of a particle impact.

14 Claims, 4 Drawing Sheets

PARTICLE DETECTION AND ANALYSIS

FIELD OF THE INVENTION

The invention relates to a method of, and apparatus for, detecting and analysing particles, and is more specifically concerned with the detection and analysis of such particles using a sensor which is responsive to particle impact.

BACKGROUND TO THE INVENTION

It is known to detect particles, such as sand, moving in a flowing fluid, for example oil, with a sensor which generates a signal in response to particle impact. Such a sensor conventionally comprises a piezo-electric element coupled to the sensor housing so that collision of particles with the housing deform the element, causing the latter to generate a voltage signal which may be analysed to obtain information on the nature of the impact.

In conventional analysis techniques, the signal is amplified, unwanted frequency components filtered-out and a thresholding procedure is then applied in order to determine whether the amplitude of the signal is greater than a pre-determined threshold level. If that threshold is passed, the detection of an impact is registered in a counter.

Since the magnitude of the sensor signal is related to the force of particle impact, a series of different threshold levels may be employed in order to give an indication of the relative magnitudes of particle impacts. The energy dissipated on impact is proportional to the momentum of the particle involved, from which an indication of the mass of the particle can be obtained if the velocity of impact is known (or deduced from, for example, the flow-rate of the fluid).

An example of such an arrangement is shown in U.S. Pat. No. 4,240,287.

One disadvantage of such an arrangement is that an accurate measure of particle size is not obtained, since the various impact signals are merely sorted into a number of ranges dictated by the threshold levels.

SUMMARY OF THE INVENTION

According to one aspect of the present invention, there is provided a method of detecting and analysing moving particles using a transducer which generates an electrical signal in response to a particle impact, having an amplitude which is related to the force of particle impact, the method comprising the steps of:

1. monitoring the instantaneous values of the transducer output signal;
2. detecting when the amplitude of the transducer output signal exceeds a given threshold and noting any local maximum values whilst the transducer output signal exceeds the said threshold;
3. determining which of a plurality of local maximum values has the overall maximum amplitude so as to discriminate between electrical noise spikes and an amplitude excursion caused by a particle impact; and
4. generating a final output signal whose amplitude corresponds to the detected local overall maximum value and whose timing bears a fixed relationship to the time at which the local overall maximum value occurred to thereby generate a signal which is indicative of the momentum and position in time of a particle impact.

Since this method provides a direct measurement of the true maximum amplitude of an excursion caused by a particle impact, a relatively accurate indication of the momentum of the associated particle may be obtained.

As mentioned the method proposed allows one to discriminate between the actual amplitude excursion produced by an impact and any amplitude excursions in the transducer oscillation which may be caused, for example, by noise.

In order to improve the overall sensitivity of the method the transducer should be only lightly damped. In this case the impact of a particle will produce a series of amplitude excursions of diminished magnitude in the transducer output signal and the time taken for these amplitude excursions to diminish to an insignificant level is called the recovery time of the transducer.

When the flux of particles incident on the transducer is relatively low it is rare for an impact to occur during the recovery time of the transducer. However, larger fluxes may cause a significant number of impacts to occur within one or more recovery times.

If a second particle impact occurs within the recovery time of the transducer the perceived amplitude of the local overall maximum value of the transducer signal for the second impact will not be an accurate measure of the momentum of the second impact due to the presence of the decaying amplitude excursions caused by the first impact.

According therefore to another aspect of the invention the method may include the step of inhibiting the transmission of any final output signal in response to any significant amplitude excursions of the transducer output signal within a period of time equal to the recovery time of the transducer after any final output signal has been generated.

This first modification of the method serves to eliminate any final output signals which are of suspect accuracy—but may inadvertently discard many impact signals, which otherwise could have been processed.

According to a further aspect of the invention the method may also include the additional step of eliminating from consideration amplitude excursions whose rise-time up to a pre-determined amplitude value is not within a preselected range of rise-times characteristic of the rise-time of an amplitude excursion resulting from a particle impact.

According to a still further aspect of the invention instead of simply rejecting amplitude excursion maxima occurring within the recovery time after a detected overall maximum amplitude value, a correction may be applied to amplitude values of the transducer output signal during the recovery time following each detected overall maximum amplitude value, to compensate for the known decaying oscillation in the output signal due to the detected impact either by adding to (or subtracting from) the detected amplitude excursion values corresponding to the known decaying oscillation before determining future overall maximum values (thereby to produce the values therefor, so that they can be accepted as the reflections of the momentum of subsequent particle impact), or modifying the output signal using a mathematical model corresponding to the known decaying waveform, so that the transmitted transducer output signal amplitude is corrected for and takes account of the previous impact, before processing to determine the next local overall maximum value.

The decaying waveform may be computed using a mathematical model which describes the oscillatory function of the damped transducer.

According to a still further aspect of the invention the time interval between adjoining overall maximum amplitude values may be determined and, using known data relating to the expected decaying waveforms from the first impact, a value of the latter at the time of occurrence of the second maximum value may be computed to allow the second maximum value to be corrected. This technique may also be used to determine whether any detected overall maximum value is due to an impact or is caused by the decaying oscillation of the transducer following an impact since all other things being equal an impact will produce a greater than expected amplitude value in the transducer output signal, given the immediate history of transducer output signal.

Whilst the whole of the signal from the transducer may be analysed continuously, preferably transducer output signals having an amplitude which lie below the threshold level are not analysed. In this way a certain proportion of electrical noise can be eliminated from the analysis, thus reducing the demands on the required processing power of the circuitry used to perform the method.

Where the transducer output signal can oscillate both positively and negatively, two thresholds may be employed, one positive and the other negative, such that only positive going excursions of a magnitude greater than the positive threshold and negative going excursions greater in magnitude that the negative threshold are available for analysis. However if, for example, only positive going excursions are to be analysed, only a positive threshold is needed and vice versa.

The invention also provides apparatus for detecting and analysing particle impacts, comprising a sensor which generates an electrical amplitude excursion in response to a particle impact, the maximum amplitude of which is related to the momentum of the particle causing the impact, a peak detector for detecting peaks in the sensor output; signal processing means for measuring the amplitude and time of occurrence of each peak; and comparator means for determining which of a series of peak values has the local overall maximum value; and output means for processing as a final output signal, a signal having a value corresponding to the locally detected overall maximum and whose timing corresponds to the time of the detected impact.

Where the sensor is of the kind in which a particle impact generates, in addition to a primary excursion, a secondary signal comprising a series of decaying amplitude excursions which attenuate to an insignificant level over a period of time corresponding to the recovery time of the sensor transducer, the apparatus preferably includes timing means for determining whether a detected overall maximum value has occurred within the recovery time immediately following a previous detected overall maximum value, and compensating means for calculating the expected value of the transducer output signal due to the first impact at the time of occurrence of the next detected overall maximum value, and adjusting the said next value to give an adjusted value which is therefore a more accurate reflection of the momentum of the second particle impact.

The methods and apparatus of the invention may include the step of (and apparatus for performing) analogue to digital conversion of the transducer output signal, at least at detected local overall maximum values, so that a digital value is available for processing.

This allows the advantages of relatively high speed analogue signal processing techniques for determining local signal maximum to be combined with the flexibility of digital processing for compensating for future values of the transducer output signal for impact accuracy within the transducer recovery periods.

BRIEF DESCRIPTION OF THE DRAWINGS

The invention will now be described by way of example only, with reference to the accompanying drawings in which.

DETAILED DESCRIPTION

The method and apparatus to be described may be used in the continuous monitoring of a flow of particular material in a fluid within an enclosed vessel in order to give an indication of size (or relative size) of particles sampled from that material.

Although the method and apparatus are described in relation to a sensor having a piezo-electric transducer (in this case a series 112A20 high resolution pressure transducer marketed by PCB Piezoelectronics), it will be apparent that the invention is not limited to such sensors, and may thus employ other types of sensor, for example piezo-inductive or piezo-resistive sensors.

Figure 1:
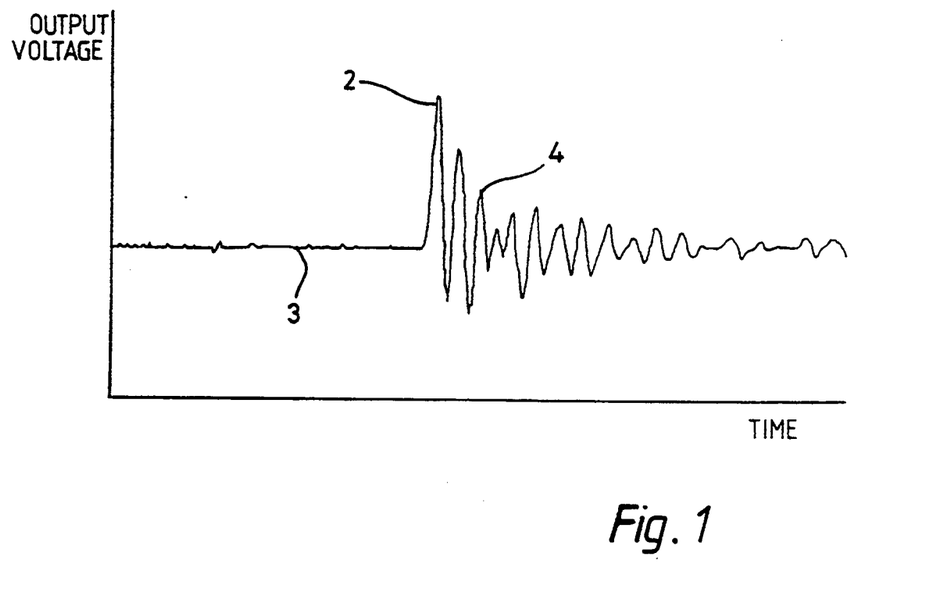
FIG. 1 shows an example of an output signal of a piezoelectric transducer which may be used in the method and apparatus according to the invention.
Figure 2:
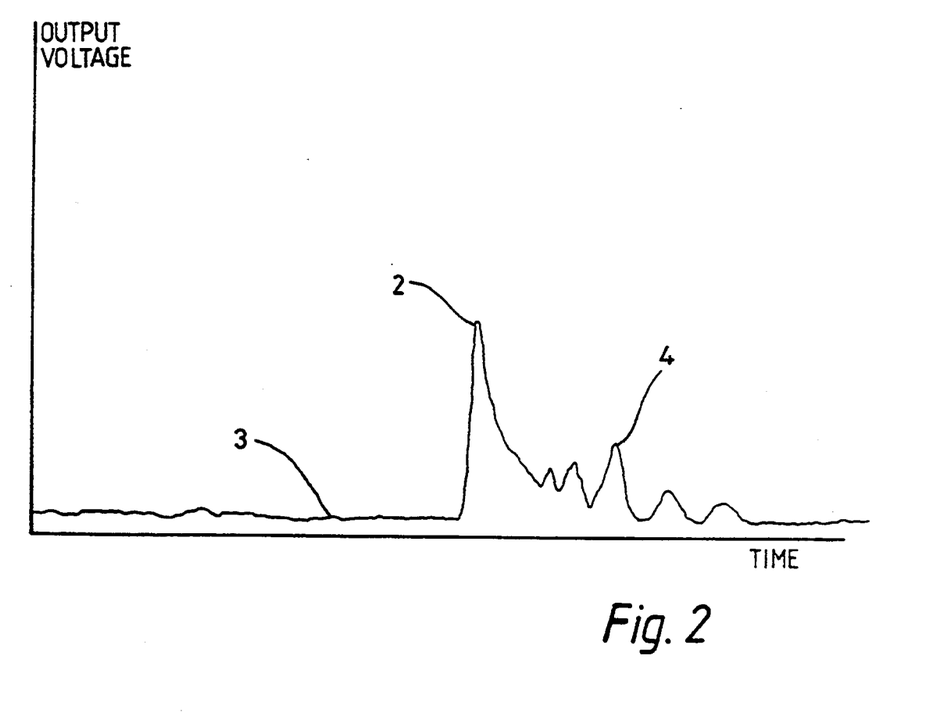
FIG. 2 shows an alternative type of output signal.

FIG. 1 illustrates a typical output wave form from a lightly damped piezo-electric transducer, showing output voltage against time following the impact of a particle. The wave form comprises a primary excursion 2 from a level 3 corresponding to a quiescent state of the sensor, followed by a series of secondary excursions, such as the excursion 4. Alternatively, the design and construction of the transducer may be such that the wave form is more heavily damped after a primary excursion, as shown in FIG. 2, in which the same reference numbers denote portions of the wave form which correspond to those of the wave form shown in FIG. 1.

In either case the magnitude of the primary excursion is substantially directly proportional to the mass of the particle which has impacted with the sensor, causing the latter to generate the signal.

In the method to be described a lightly damped transducer is used.

The method involves monitoring the waveform in order to identify the rapid rise time to the peak value which is a characteristic of the transducer's output following a particle impact. This rise time is related to the resonant frequency of the transducer and is typically of the order of 1 to 2 microseconds. The expected rise time of the output signal for a given transducer will normally be provided as part of the manufacturer's data. Knowing the expected rise time, it is then possible to exclude those parts of the waveform which have a signal rise time outside a defined band of acceptable values around the expected rise time. Noise which is most likely to be present at lower frequencies compared to the transducer's output may therefore be discriminated out in subsequent processing of the rise time data.

The second feature of the transducer's waveform which is monitored is the magnitude of the initial peak following an impact. To maximize the accuracy of this measurement, a very high-speed peak detector and analogue to digital converter are used. This ensures that the waveform is sampled and digitized close to the peak.

Figure 3:
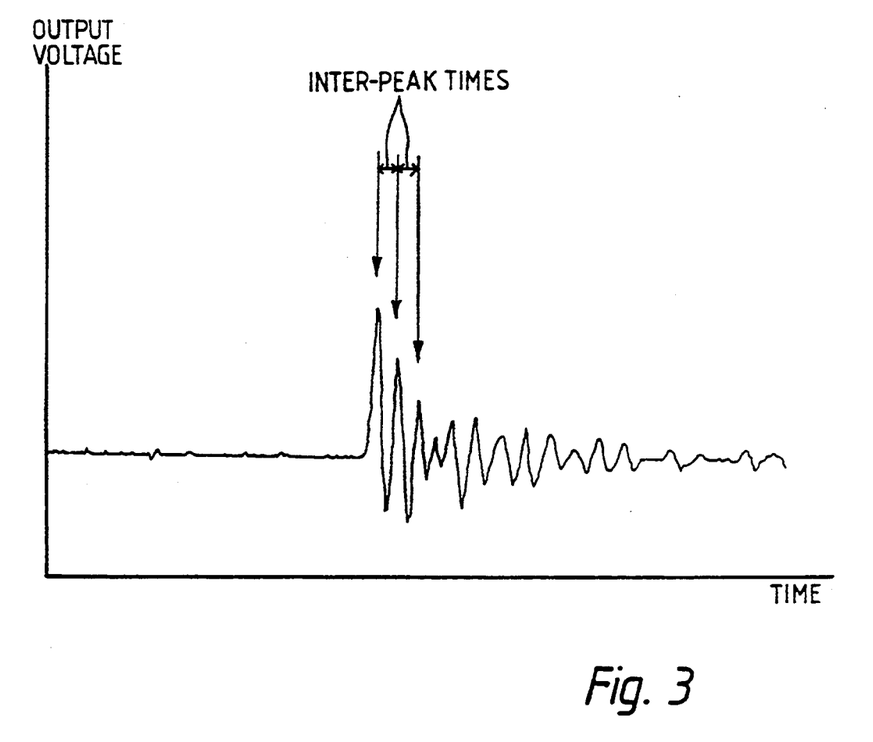
FIG. 3 illustrates one of the analysis techniques to be used on an output signal such as is shown in FIG. 1.

The method may also involve the measurement of the time intervals between successive peaks in the waveform as indicated in FIG. 3. The transducer's waveform consists of a series of steadily reducing secondary peaks as the resonance effect within the transducer decays. This gives a series of equally spaced peaks, the time interval between the peaks being dependent upon the resonant frequency of the transducer. After the final peak there would be a quiescent period until the next impact occurred. This timing information may be used to determine if sufficient time, ie. the recovery time, has elapsed since the previous impact for the waveform to return to its quiescent state. Alternatively the system may determine whether the recovery time (which is dependent upon the intrinsic characteristics of the transducer and hence may be predetermined) has elapsed by determining whether the time interval between the previous impact peak and a subsequently detected peak is greater or less than the recovery time.

If successive impacts occur in less time than is allowed for the waveform to settle to its quiescent level, which is typically 75 to 100 miscroseconds after the first peak is detected, then the peak value relating to the next impact may need to be discounted, or corrected.

Figure 5:
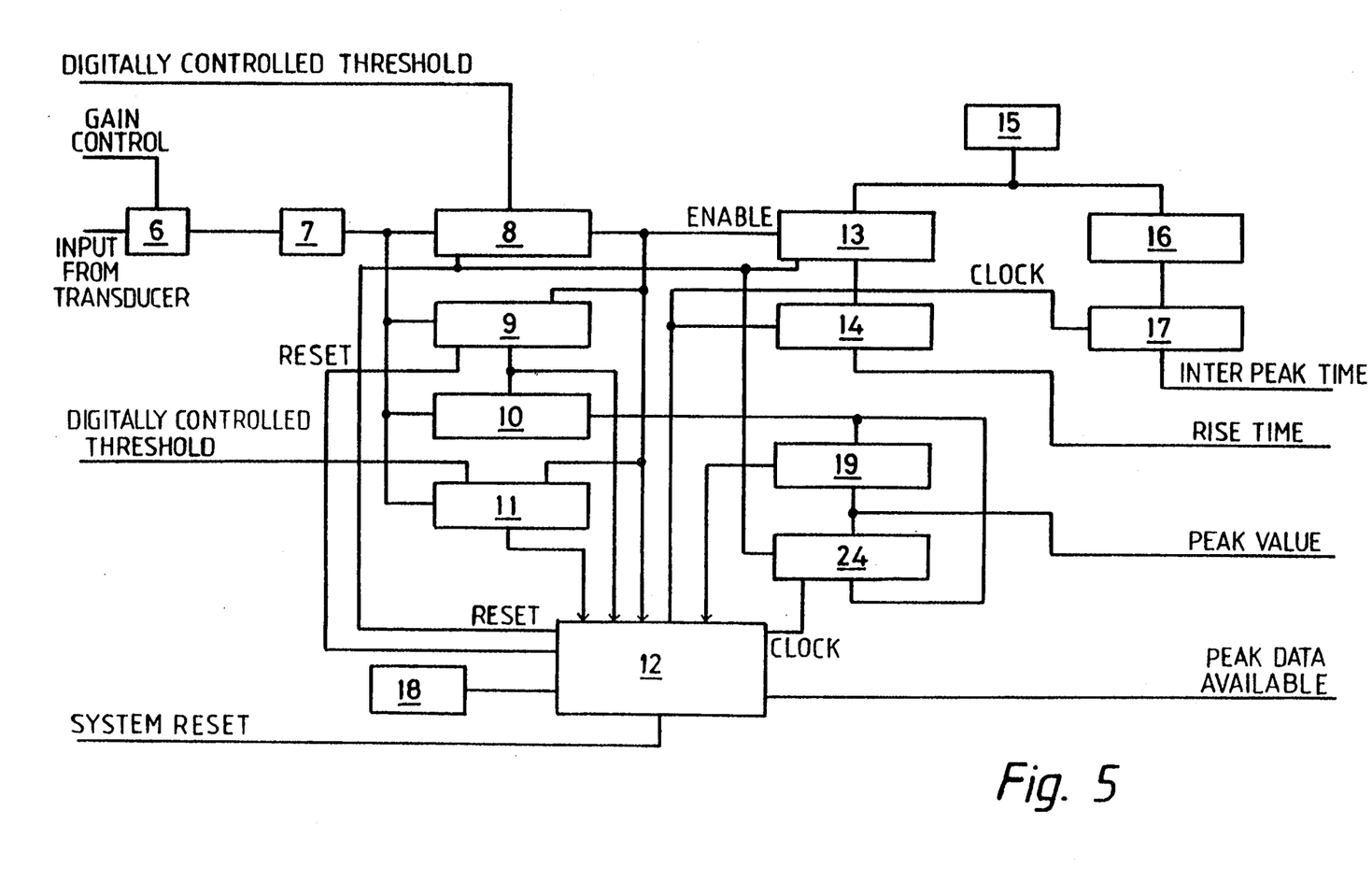
FIG. 5 is a block diagram of apparatus according to the invention.

Referring to FIG. 5, apparatus for carrying out this method comprises an instrumentation amplifier 6 connected to a unity gain buffer 7. The output of the buffer 7 is, in turn, connected in parallel to a front threshold detector 8, a peak detector 9, an analogue to digital convertor (ADC) 10 and a rear threshold detector 11. The apparatus also includes a rise time counter 13 having an input connected to the threshold detector and an output connected to a rise time register 14.

The output of the detector 8 is connected in parallel to the peak detector 9, the rise time counter 13, the rear threshold detector 11 and an input of a control unit 12. The output of the detector 9 is connected in parallel to the converter 10 and to an input of the unit 12, another input of which is connected to the output of the rear threshold detector 11.

The threshold detectors 8 and 11 may be digitally controlled by suitable signals generated by for example manual control means (not shown) and fed to the detectors along the lines labelled "Digitally controlled threshold" similarily the separate control means may be used to control the gain of the amplifier 6 or to reset the system by means of signals fed respectively to the amplifier 6 and unit 12 along the designated lines.

The rise time counter 13 and hence the rise time register 14 are controlled by time impulses generated by a clock 15, which also controls an inter-peak counter 16 and associated inter-peak time register 17. The components 13 and 14, are operable to measure and store the rise-time of a detected excursion. The components 16 and 17 are operable to measure and store as indication of the time of occurance of maximum amplitude peaks, which measurements can then be processed to give a measure of the time delay between successive maximum amplitude peaks (i.e. the inter peak timing).

The magnitudes of the peaks in a detected excursion are analysed by a comparator 19 and a peak-value register 24, both of which are connected to the output of the ADC. The comparator 19 is also connected to an input of the control unit 12, which is also connected to a clock 18, and can generate a reset signal which resets the threshold detector 8, the peak detector 9, the rise-time counter 13 and the peak-value register 24.

The unit 12 has an output connected (along a line marked clock) to the rise time register 14 an inter-peak register 17, so that a signal generated by the unit 12 at the output causes values from the rise time register and inter peak counter to be latched into the registers 14 and 17 respectively.

A similar function is performed by a signal from another output of the unit (along the second line marked 'clock') 12 which is connected to the register 24 so that the signal causes a value from the converter 10 to be latched into the register 24.

The remaining output of the unit 12 is connected to processor means (not shown) which, on receipt of "peak data available" signal from that output, records the values latched in the registers 14, 17 and 24, to all of which the processor means is also connected.

The threshold detectors 8 and 11 enable the apparatus to function without having to track the waveform of the sensor signal continuously. This is of particular advantage in the absence of any impact upon the sensor when only low amplitude noise would be present.

The first or front threshold detector 8 is used to enable the sampling circuitry of the apparatus only when the signal exceeds the level at which the detectors 8 is set. The second or rear threshold detector 11 determines when the signal has fallen below a defined level and causes the sampling circuitry to be disabled. The use of threshold detectors helps to minimize the amount of data captured by the system and simplifies the subsequent processing requirements.

Figure 4:
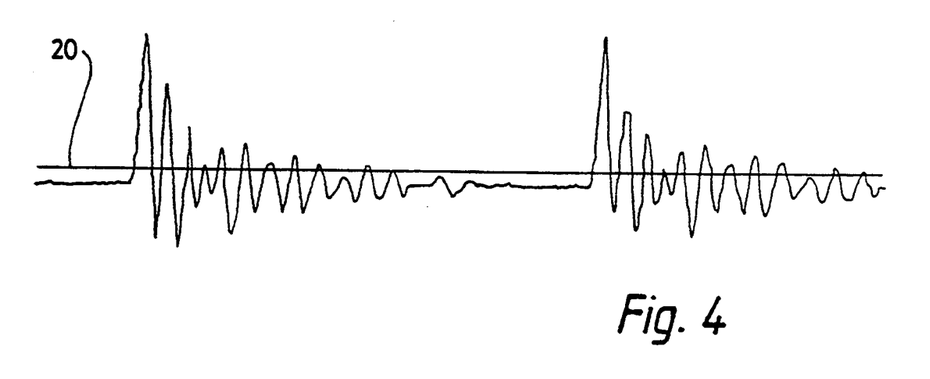
FIG. 4 illustrates another aspect of the analysis of a sensor output.

In normal operation the front threshold detector 8 is set at a level which is slightly above the background noise which exists in the system. Any noise which exceeds the front threshold level is tracked by the peak detector 9. However, it normally would be rejected in subsequent processing of the sampled data because its rise time is unlikely to be characteristic of that of a particle impact. The level of the rear threshold detector 11 is usually set to the same level as the front threshold detector 8. FIG. 4 shows a threshold level 20 for the front and rear detectors superimposed upon the waveform. The operation of the apparatus will now be described, in overview, in relation to the signal shown in FIG. 4.

Initially the signal level is lower than the threshold 20 of the front detector 8. When an impact occurs the signal level rises rapidly and exceeds the front detector's threshold. This, causes the high-speed counter 13 and the high speed peak detector 9 to be enabled. The counter 13 acts as a rise-time counter which is fed from the clock 15, and is used to time the rising edge of the waveform following an impact. The high-speed peak detector 9 becomes operable to detect positive-going peaks on the transducer's waveform. When such a peak is detected, the peak detector 9 triggers the analogue to digital converter 10 to sample and digitize the signal level at the detected peak points. The peak detector 9 continues to monitor the waveform until its amplitude falls below the threshold 20 on the rear threshold detector 11.

During operation, the register 24 will retain the value of the highest peak encountered in the current cycle (ie while the threshold 20 is exceeded by the signal). The rise-time register 14 will hold the number of clock periods which have occurred since the counter was enabled up to the point when the highest magnitude peak is detected, and the register 17 holds the total number of clock periods which have occurred since the apparatus was put operation, which can be used to provide inter-peak timing information.

The information held in the two registers and the peak value sampled by the analogue to digital converter 10 are relayed to a processor (not shown) for storage and analysis when the signal level has gone below that set on the rear threshold detector.

The operation of the apparatus will now be described in detail.

The transducer's output is fed into the instrumentation amplifier 6, the gain of which is digitally controlled from the processor unit. This allows the transducer's output signal to be scaled appropriately to match the reference voltage on the analogue to digital converter. This assists in minimizing the conversion error, particularly when dealing with low amplitude signals. Instrumentation amplifiers also possess excellent noise rejection characteristics because of their differential inputs. This is an advantage when dealing with signals from a transducer which may be located at some distance from the sampling hardware.

The output of the instrumentation amplifier 6 is fed into the unity-gain buffer 7 which isolates it from the capacitive load in the high-speed peak detector. The output signal from the buffer is supplied to four analogue subsystems i.e. the front threshold detector 8, the high-speed peak detector 9, the analogue to digital converter 10, and the rear threshold detector 11. The threshold detectors are designed around high-speed comparators with one input from the buffered signal and the other from digitally controlled potentiometers (not shown). These are controlled from the processor unit and allow a wide range of threshold conditions to be selected.

The hardware design ensures that there are interlocks upon the operation of the analogue sub-systems. Therefore the peak detector circuitry is not active until enabled by the front threshold detector 8. The rear threshold detector 11 is also enabled by the front threshold detector 9.

When the buffered signal exceeds the front threshold level, the detector is activated, and will remain in that state until cleared by a reset from the control unit 12. Once enabled, the peak detector tracks the input signal by using a diode-clamped differentiator. As a peak is reached and then begins to reduce, the direction of current flowing in the detector's capacitor reverses. This in turn causes the output of the differentiator's operational amplifier to change its output state very rapidly. A high-speed comparator detects this change and causes the output state of the peak detector 9 to be latched up. The comparator also generates an edge trigger output which is used as a clock edge for two purposes.

Firstly, it triggers the high-speed analogue to digital converter 10 which samples the buffered signal and latches its digital output within 50 nanoseconds. Secondly, it initiates sequencing logic programmed into the control unit 12 which then samples the output of the comparator 19 after a short delay. Some excursions possess more than one peak before the signal falls below the rear threshold level. The peak detector 9 detects each such peak, which is also analysed by the ADC 10, but the apparatus retains just the highest peak value together with the associated timing information from the timing counters.

This is achieved by comparing the new peak value with the previous peak, if any, in the current impact signal. Any previous peak value is latched up in the peak value register 24, the input of which is connected to the analogue to digital converter's output. The peak value register 24 is cleared prior to the front threshold detector being enabled by a reset signal from the sequencing logic of the unit 12. Therefore with the initial peak value of an impact, the analogue to digital output peak value will exceed the null state of the peak value register 24. The sequencing logic will cause the analogue to digital output to be latched into the peak value register 24. In addition it will cause the rise-time register 14 and inter-peak time register 17 to be loaded from their respective counters. The rise-time register 14 will then hold the number of timing pulses accumulated by the rise-time counter since the front threshold detector became enabled.

The inter-peak counter 16 is clocked with timing pulses from the same source as the rise-time counter 13. It is not controlled by a reset signal, but is allowed to clear itself by overflowing before incrementing again. The inter-peak time register 17 provides information regarding the position of peaks in time relative to its counter. Thus the value latched into the register 17 will be directly related to the time elapsed since the front threshold was first exceeded, because the counter 16 does not stop when the signal falls below the threshold 20 in the interim. Consequently an indication of the inter peak timing may be obtained by subtracting consecutive values entered into the processor from the register 17.

Having loaded the peak value and timing registers, the sequencing logic re-enables the peak detector circuitry.

If another peak is detected before the rear threshold level 20 is reached the sequencing cycle is repeated. If the new peak value does not exceed the stored in the peak value register 24 it is discarded and the timing registers are not reloaded but retain the previously loaded values associated with the peak value in the peak value register. If the new peak value does exceed the value stored in the peak value register it is transferred into that register and the two timing registers are loaded from their respective counters.

When the input signal falls below the rear threshold level 20, the sequencing logic generates a data available signal to the processor unit. The contents of the registers holding the peak value, the rise time and inter-peak time can then be read by the processor (not shown). The monitoring hardware is only re-enabled when the processor has read the registers and issued a system reset which reinitializes the hardware.

The processor unit then analyses the data from the Registers to determine whether the rise time of the peak falls within a predetermined band of acceptable values. The peak is discounted if its rise time is not within that band.

Where a peak, which has not occurred in the recovery time of the sensor, has an acceptable rise time, the processor unit generates a final output signal indicative of the momentum and time of occurrence of the impact.

The processor unit also uses the time of occurrence of the peak to mark the start of the recovery time (which is already known). During the recovery time, the information supplied to the processor may relate to a secondary peak caused by the resonance effect within the transducer or a peak resulting from a further impact.

The magnitudes and times of occurrence of the secondary peaks are dependent upon the characteristics of the transducer, and can be predicted by the processor unit using a suitable mathematical model.

In order to distinguish between the two different types of peak, the processor first compares the time of occurrence of the detected peak with predicted times of occurrence of the secondary peak. If the detected peak has not occurred at one of these predicted times, the processor treats the peak as having been caused by an impact.

Where the peak occurred at a time which coincides with a predicted secondary peak time, the processor then compares the magnitude of the peak with the predicted magnitude of the secondary peak in question. If the detected magnitude is significantly greater than the predicted magnitude, the peak is also treated as having been caused by an impact. Otherwise, the processor treats the peak as a secondary peak, and consequently does not generate a final signal.

In the event that the peak is treated as having been caused by an impact, the processor unit uses the time of occurrence to mark the start of a further recovery time for use in connection with the analysis of subsequent peaks, and may then apply a correction to the peak value before generating a final signal, or alternatively may discount the peak.

In a simplified embodiment, intended for use in situations in which impacts are unlikely to occur within recovery times, the processor unit simply discounts all the peaks which are detected in a recovery time following an initial peak, since these are most likely to be secondary peaks.

In order that this system may be used over extended operating periods it is preferable that any dc drift of the analogue signal be detected and corrected. This drift would have the effect of increasing or reducing the apparent amplitude of an impact. This type of drift is principally associated with temperature variations. As the transducer may incorporate electronic circuitry and is likely to be affected by temperature changes in the fluid, it is important that the transducer should be in circuit when assessing the extent of the dc drift. To avoid removing the transducer from its monitoring position it may, in some circumstances, be possible to suspend the fluid flow to measure the dc level in the absence of particle impacts. Alternatively, in situations where this is impossible, the processor unit could generate a periodic control signal to activate a screen to protect the face of the transducer from the fluid flow. Typically this would be based upon an electro-mechanical system using a solenoid carrying a small screen.

Figure 5A:
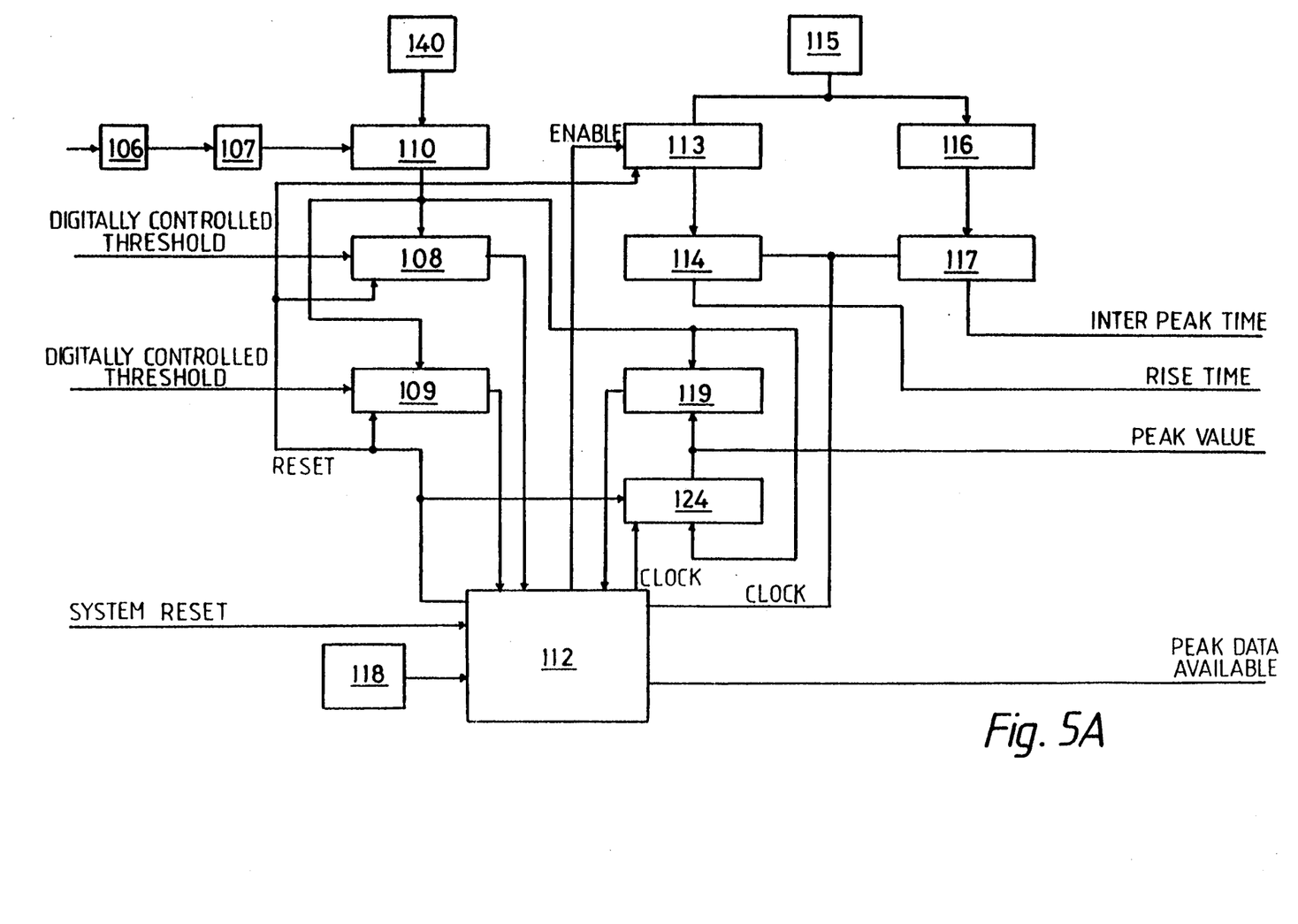
FIG. 5A shows a modified version of the apparatus of FIG. 5.

In FIG. 5A, components corresponding to components shown in FIG. 5 are denoted by the associated reference numbers FIG. 5 increased by one hundred.

The apparatus shown in FIG. 5 does not have a peak detector. Instead, the Analogue to Digital converter, one input of which is connected to the amplifier 106 through the buffer 107, continuously converts the signal fed to the input into digital form under the control of a sampling clock 140 connected to the clock input of the converter 110.

The digital signal produced by the converter 110 is relayed to digital front and rear threshold detectors 108 and 109 and to the comparator and peak value register 119 and 124.

As with the apparatus of FIG. 5, the threshold levels of the detectors 108 and 109 may be set and adjusted using control means (not shown) which are connected to the inputs indicated by the "Digitally controlled threshold" lines.

The outputs of the detectors 108 and 109 are connected to inputs of the control until 112, which in response to a signal from the detector 108 (indicating that the front threshold has been exceeded) generates at one output an enable signal for the rise time counter 113, and in response to a signal from the detector 109 generates at another output a reset signal for the detectors 108 and 109, and the counter 113.

The unit 112 includes a system reset input connected to the control means input for the clock 118, and an input for a signal from the comparator 119. One of the two outputs of the unit 112 indicated by the lines labelled 'clock' is connected to the register 124, whilst the other is connected to the rise time and inter peak time registers 114 and 117. The unit may generate signals at those outputs to cause appropriate values to be latched into the registers 114, 117 and 124.

A clock 115 regulates the counter 113 and the inter peak counter 116. The outputs of registers 114, 117 and 124 are connected to processing means (not shown) which, on receipt of a 'peak data available' signal from the associated output of the unit 112, reads the "inter-peak time", rise time and peak value latched into the registers at that time.

The front threshold detector 189 includes a control register, which can be loaded from the processing unit, and a high-speed digital comparator. As before, the purpose of the front threshold detector is to determine when the amplitude of the input signal exceeds the threshold value specified by the contents of the control register.

When the input signal has an amplitude lower than the threshold level, the comparator in the front threshold detector 108 ensures that the peak value circuit is disabled. For every analogue to digital conversion cycle the comparator compares the resultant digital output with the threshold value in the control register. Only when the comparator detects that the analogue to digital output has exceeded the front threshold level does it switch an output signal which is received by the unit 112 which in turn, enables the counter 113. The front threshold detector 108 is then itself disabled until the rear threshold detector 109 detects the input signal falling below the associated threshold.

The rear threshold detector 109 also comprises a control register and high-speed comparator. As with the front threshold detector 108, its control register is loaded with the relevant threshold value by the processor unit. The mode of operation of this detector is similar to the front threshold detector 108, except that its comparator switches an output signal (to the unit 112) which is used to disable the peak-value circuit when the analogue to digital output falls below the value stored in its control register.

Because the analogue to digital converter 110 is continuously digitising the input waveform, the comparator 119 and register 114 are used to examine all of the digitised samples of the waveform between the threshold levels.

The peak-value register 124 is initialised to zero prior to the front threshold level being reached.

The comparator 119 compares each digitised sample with the highest peak value found during the current cycle (ie while the threshold is exceeded) and the system retains the higher of the two in the peak-value register. Consequently, when digitised waveform falls so as to activate the rear threshold detector 109, the value remaining in the peak-value register 124 will be the highest encountered in the current cycle.

With the clock 140 operating at a frequency of 20 MHz a digital sample of the waveform would be available every 50 nS. For the present embodiment, this provides a sufficiently high sampling rate for the type of waveform being monitored, although higher rates may be required for relatively large fluxes of particles.

In the FIG. 5A arrangement, the operation of the rise-time and inter-peak time counters is identical to that previously described in relation to FIG. 5.

Sequencer and Synchronization Logic Relating to FIG. 5

The sequencer and synchronization logic of the design is based upon a programmable logic sequencer which provides a Mealy state machine with a registered output. The PLS105 sequencer from Advanced Micro Devices offers an AND/OR logic structure. The AND and OR arrays are both programmable to allow implementation of the sum-of-products equations.

The AND array can support up to 16 external inputs. The input signals which are applied to this array are: the output from the front threshold detector which indicates when the analogue input signal has exceeded the front threshold level, the output from the rear threshold detector which indicates when the analogue signal has fallen below the rear threshold level, the output signal from the peak detector circuit indicating that a peak has been detected, the system reset signal which is supplied from the main processor unit, the output from the comparator comparing the A to D output with the value stored in the peak-value register and a sequencer clock signal generated by an oscillator module.

The OR array of the sequencer drives eight output registers and six buried state registers. The output registers are used to provide the following output signals: a local reset signal to reset the peak detector, another independent reset signal to reset or clear the rise-time register and peak-value register, a clock signal to strobe the rise-time register and inter-peak register, a clock signal to strobe the peak-value register and a peak data-available signal which is routed to the main processor unit.

Sequencer and Synchronization Logic Relating to FIG. 5A

The sequencer and synchronization logic relating to FIG. 5A is similar to that described for FIG. 5. the PLS105 sequencer carries out the same functions except that the peak detector input signal is removed. The role of the peak detector input signal is in effect carried out by the signal generated by the comparator associated with the peak-value register.

| Principal hardware components | | |
|---|---|---|
| Implementation: | FIG. 5 | FIG. 5A |
| Instrumentation Amplifier | PGA202 | PGA202 |
| Unity gain buffer | AD847 | AD847 |
| Front threshold detector | AM686 | 74AS885 |
| Rear threshold detector | AM686 | 74AS885 |
| Peak detector | OPA600 | — |
| A to D converter | MC10319 | MC10319 |
| Rise-time counter | 74AS867 | 74AS867 |
| Inter-peak time counter | 74AS867 | 74AS867 |
| Rise-time register | 74F374 | 74F374 |
| Inter-peak time register | 74F374 | 74F374 |
| Comparator | 74AS885 | 74AS885 |
| Peak-value register | 74ALS273 | 74ALS273 |
| Sequencer | PLS105 | PLS105 |

A limited number of additional AND and NOR gates are also used to provide basic logical functions.

I claim:

1. A method of detecting and analysing moving particles using a transducer which generates an electrical signal in response to a particle impact, having an amplitude which is related to the force of particle impact, the method comprising the steps of:
   a. monitoring the instantaneous values of the transducer output signal;
   b. detecting when the amplitude of the transducer output signal exceeds a given threshold and noting any local maximum values whilst the transducer output signal exceeds the said threshold;
   c. determining which of a plurality of local maximum values has the overall maximum amplitude so as to discriminate between electrical noise spikes and an amplitude excursion caused by a particle impact; and
   d. generating a final output signal whose amplitude corresponds to the detected local overall maximum value and whose timing bears a fixed relationship to the time at which the local overall maximum value occured to thereby generate a signal which is indicative of the momentum and position in time of a particle impact.

2. A method according to claim 1 in which the transducer has associated with it a recovery time and wherein the method includes the further step of inhibiting the transmission of any final output signal in response to any significant amplitude excursions of the transducer output signal within a period of time equal to the recovery time of the transducer after any final output signal has been generated.

3. A method according to claim 1 in which the method includes the additional steps of determining the rise times of said local maximum value and of eliminating from consideration amplitude excursions whose rise-time up to a pre-determined amplitude value is not within a preselected range of rise-times characteristic of the rise-time of an amplitude excursion resulting from a particle impact.

4. A method according to claim 1 in which the method includes the steps of determining the rise times of said local maximum values and applying a correction to amplitude values of the transducer output signal during the recovery time following each detected overall maximum amplitude value, to compensate for the known decaying oscillation in signal of the transducer due to the detected impact either by adding to (or subtracting from) the detected amplitude excursion values corresponding to the known decaying oscillation before determining future overall maximum values.

5. A method according to claim 1 in which the method includes the steps of determining the rise times of said local maximum values and modifying the output signal using a mathematical model corresponding to the known decaying waveform, so that the transmitted transducer output signal amplitude is corrected for and takes account of the previous impact, before processing to determine the next local overall maximum value.

6. A method according to claim 5 in which the mathematical model describes the oscillatory function of the damped transducer.

7. A method according to claim 4 in which the time interval between adjoining overall maximum amplitude values is determined and, using known data relating to the expected decaying waveforms from the first impact, a value of the latter at the time of occurrence of the second maximum value is computed to allow the second maximum value to be corrected.

8. A method according to claim 1 in which the peaks in the transducer output signals having an amplitude which lie below the threshold level are not analysed.

9. A method according to claim 1 in which two thresholds are employed, one positive and the other negative, such that only positive going excursions of a magnitude greater than the positive threshold and negative going excursions greater in magnitude that the negative threshold are available for analysis.

10. A method according to claim 1 in which the analogue output signal from the transducer is converted into digital form in the region of the detected maximum values.

11. Apparatus for detecting and analysing particle impacts, comprising a sensor which generates an electrical amplitude excursion in response to a particle impact, the maximum amplitude of which is related to the momentum of the particle causing the impact; a peak detector for detecting peaks in the sensor output; signal processing means for measuring the amplitude and time of occurrence of each peak; comparator means for determining which of a series of peak values has the local overall maximum value; and output means for processing as a final output signal, a signal having a value corresponding to the locally detected overall maximum and whose timing corresponds to the time of the detected impact.

12. Apparatus according to claim 11 in which the sensor is lightly damped so that a particle impact causes the sensor to generate, in addition to a primary excursion, a secondary signal comprising a series of decaying amplitude excursions which attenuate to an insignificant level over a period of time corresponding to the recovery time of the sensor transducer, the apparatus including timing means for determining whether a detected overall maximum value has occurred within the recovery time immediately following a previous detected overall maximum value.

13. Apparatus according to claim 11, further comprising compensating means for calculating the expected value of the transducer output signal due to the first impact at the time of occurrence of the next detected overall maximum value, and adjusting the said next value to give an adjusted value which is therefore a more accurate reflection of the momentum of the second particle impact.

14. Apparatus according to claim 11 in which the apparatus includes the apparatus for performing analogue to digital conversion of the transducer output signal, at least at detected local overall maximum values, so that a digital value is available for processing.

* * * * *